US 11,905,316 B2

(12) United States Patent
Yuan et al.

(10) Patent No.: US 11,905,316 B2
(45) Date of Patent: Feb. 20, 2024

(54) APPLICATIONS OF ZMROA1 PROTEIN IN REGULATING PLANT DENSITY TOLERANCE

(71) Applicant: China Agricultural University, Beijing (CN)

(72) Inventors: Lixing Yuan, Beijing (CN); Zheng Zhao, Beijing (CN); Kunhui He, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 18/316,371

(22) Filed: May 12, 2023

(65) Prior Publication Data
US 2023/0382959 A1 Nov. 30, 2023

(30) Foreign Application Priority Data
May 24, 2022 (CN) .......................... 202210569763.2

(51) Int. Cl.
C07K 14/41 (2006.01)
C12N 15/82 (2006.01)
C07K 14/415 (2006.01)

(52) U.S. Cl.
CPC ........ *C07K 14/415* (2013.01); *C12N 15/8262* (2013.01); *C12N 15/8271* (2013.01)

(58) Field of Classification Search
None
See application file for complete search history.

(56) References Cited

U.S. PATENT DOCUMENTS

2012/0317678 A1* 12/2012 Uga ................... C12N 15/8273
435/6.12
2021/0324397 A1 10/2021 Zhang et al.

FOREIGN PATENT DOCUMENTS

| CN | 102906267 A | 1/2013 |
|---|---|---|
| CN | 102918154 A | 2/2013 |
| CN | 110563827 A | 12/2019 |
| CN | 112048010 A | 12/2020 |
| WO | 2021147401 A1 | 7/2021 |

OTHER PUBLICATIONS

Meaning of word "regulating" in Merriam-Webster dictionary. https://www.merriam-webster.com/dictionary/regulating. Accessed Jul. 10, 2023. (Year: 2023).*
Meaning of word "derive" in Merriam-Webster dictionary. https://www.merriam-webster.com/dictionary/derive. Accessed Jul. 10, 2023. (Year: 2023).*
Hammer et al., 2009, Can changes in canopy and/or root system architecture explain historical maize yield trends in the US corn belt?. Crop Science, 49(1), 299-31. (Year: 2009).*
Roy et al., 2000, Evolutionary dynamics of pathogen resistance and tolerance. Evolution, 54(1), 51-63. (Year: 2000).*
Feng et al., 2022, ABA-inducible Deeper Rooting 1 improves adaptation of maize to water deficiency. Plant Biotechnology Journal, 20(11), 2077-2088 (Year: 2022).*
Assefa et al., 2018, Analysis of long term study indicates both agronomic optimal plant density and increase maize yield per plant contributed to yield gain. Scientific Reports, 8(1), 4937. (Year: 2018).*
MaizeGDB Gene Record Page: Zm00001eb314060. https://www.maizegdb.org/gene_center/gene/Zm00001eb314060. Accessed Jul. 9, 2023. (Year: 2023).*
Feng et al., 2022, ABA-inducible Deeper Rooting 1 improves adaptation of maize to water deficiency, Supplementary Figure 003. Plant Biotechnology Journal, 20(11), 2077-2088 (Year: 2022).*
Feng et al., 2022, ABA-inducible Deeper Rooting 1 improves adaptation of maize to water deficiency, Supplementary Figure 007. Plant Biotechnology Journal, 20(11), 2077-2088 (Year: 2023).*
Zheng et al., 2023, Local auxin biosynthesis regulates brace root angle and lodging resistance in maize. New Phytologist, 238(1), 142-154. (Year: 2023).*
Uga et al., 2013, Control of root system architecture by Deeper Rooting 1 increases rice yield under drought conditions. Nature genetics, 45(9), 1097-1102 (Year: 2013).*
Uga et al., 2013, Control of root system architecture by Deeper Rooting 1 increases rice yield under drought conditions, Supplementary data. Nature genetics, 45(9), 1097-1102 (Year: 2013).*
Jiang Da-Long, et al., Correlations Between Characters of Roots and Those of Aerial Parts of Maize in Different Plant Type, Seeds, 2014, pp. 94-96, vol. 33, No. 7.
XM_008654549.3, Predicted: *Zea mays* uncharacterized LOC103632815(LOC103632815), mRNA, GenBank, 2020.
XP_008652771.1, uncharacterized protein LOC103632815 [*Zea mays*], GenPept, 2020.
Paolo A. Sabelli, et al., cDNA and promoter sequences for MCM3 homologues from maize, and protein localization in cycling cells, Journal of Experimental Botany, 1999, pp. 1315-1322, vol. 50, No. 337.

\* cited by examiner

*Primary Examiner* — Charles Logsdon
*Assistant Examiner* — Santosh Sharma
(74) *Attorney, Agent, or Firm* — Bayramoglu Law Offices LLC (57) ABSTRACT

Applications of a ZmROA1 protein or substance regulating the content or activity of the ZmROA1 protein are provided. The ZmROA1 protein can be specified as follows: A1), A2) or A3): A1, the amino acid sequence is the amino acid sequence shown in SEQ ID NO: 3; A2, the protein, which is obtained by replacing and/or deleting and/or adding the amino acid sequence shown in SEQ ID NO: 3 through amino acid residues, is more than 80% identity to A1) and relates to plant root angle; A3, the fusion protein which is obtained by linking N-end or/and C-end of A1) or A2) to protein tags. ZmROA1 protein and its related biological materials can be used to regulate plant density tolerance and/or root angle, and the cultivation of new density-tolerant maize varieties, which helps improve maize harvest index for high and stable yield.

1 Claim, 5 Drawing Sheets
Specification includes a Sequence Listing.

| Treatment | Genotypes | Ear length (cm) | Ear width (cm) | Kernel weight (g) | Weight (g/100Kernels) | Volume (kg/L) | Ear row number | Kernels number/row | Ear barren tip length(cm) |
|---|---|---|---|---|---|---|---|---|---|
| | WT | 13.94±0.68 | 3.64±0.09 | 45.85±6.26 | 20.73±2.93 | 0.69±0.04 | 15.20±1.10 | 21.40±2.97 | 3.24±0.26 |
| LD | OE-ZmROA1-3 | 12.88±0.66* | 3.33±0.23* | 39.88±7.52 | 20.75±2.36 | 0.72±0.01 | 14.00±1.41 | 20.00±3.46 | 2.88±0.58 |
| | OE-ZmROA1-4 | 14.08±0.43 | 3.58±0.08 | 46.21±7.60 | 22.50±2.59 | 0.70±0.01 | 14.40±1.67 | 19.80±1.48 | 2.88±0.68 |
| Treatment | Genotypes | Ear length (cm) | Ear width (cm) | Kernel weight (g) | Weight (g/100Kernels) | Volume (kg/L) | Ear row number | Kernels number/row | Ear barren tip length(cm) |
| | WT | 12.02±1.09 | 3.51±0.32 | 38.83±6.23 | 20.12±2.13 | 0.70±0.007 | 14.00±2.00 | 20.80±1.79 | 2.46±0.46 |
| MD | OE-ZmROA1-3 | 12.48±1.15 | 3.68±0.13 | 35.50±12.97 | 21.20±1.67 | 0.68±0.02 | 14.40±2.19 | 17.40±3.97 | 2.84±0.23 |
| | OE-ZmROA1-4 | 13.86±0.44** | 3.70±0.07 | 41.51±3.72 | 21.05±2.79 | 0.67±0.02** | 13.60±0.89 | 20.00±2.45 | 2.62±0.73 |
| Treatment | Genotypes | Ear length (cm) | Ear width (cm) | Kernel weight (g) | Weight (g/100Kernels) | Volume (kg/L) | Ear row number | Kernels number/row | Ear barren tip length(cm) |
| | WT | 11.84±0.81 | 3.24±0.34 | 27.05±9.41 | 21.47±1.85 | 0.70±0.06 | 11.60±0.89 | 18.60±3.78 | 3.10±0.59 |
| HD | OE-ZmROA1-3 | 11.2±0.78 | 3.50±0.20 | 33.50±6.72 | 20.65±2.05 | 0.63±0.10 | 12.67±1.15 | 17.67±1.53 | 2.20±0.20* |
| | OE-ZmROA1-4 | 12.06±0.99 | 3.42±0.13 | 33.00±8.79 | 21.15±2.48 | 0.70±0.01 | 13.20±1.10* | 20.00±3.39 | 2.44±0.43 |

APPLICATIONS OF ZMROA1 PROTEIN IN REGULATING PLANT DENSITY TOLERANCE

CROSS REFERENCE TO THE RELATED APPLICATIONS

This application is based upon and claims priority to Chinese Patent Application No. 202210569763.2, filed on May 24, 2022, the entire contents of which are incorporated herein by reference.

Sequence Listing

The instant application contains a Sequence Listing which has been submitted in XML format via EFS-Web and is hereby incorporated by reference in its entirety. Said XML copy is named GBZYGJ103_Sequence_Listing.xml, created on May 8, 2023, and is 18,809 bytes in size.

TECHNICAL FIELD

The invention relates to applications of ZmROA1 protein in regulating the density tolerance of plants in the field of biotechnology.

BACKGROUND

Maize (*Zea mays* L.) is a very important crop worldwide as food, fodder, biofuel and industrial raw materials. Maize production has accounted for 38% of the total cereal production in the world (FAO.,2019). Variety improvement and field management optimization jointly promote the increase of maize grain yield (Duvick et al., 2005; lee et al., 2007). Among them, the increasing maize planting density has become an important strategy to ensure food security in the future (Lashkari et al., 2011). Breeding density-tolerant varieties and rational close planting are demonstrated to be a feasible strategy to improve maize yield.

The root plays an important role in plant acquisition of soil resources, plant growth and yield formation. Root system architecture determines the spatial and temporal distribution of roots in specific soil areas and their ability to obtain nutrient and water resources (Lynch, 2019). Root growth angle will affect the three-dimensional root distribution in the soil and therefore has an overall effect on the dense planting space of maize. Steep growth angles tend to have deeper roots, and deep rooting can improve water and nitrogen use efficiency and reduce root-to-root competition (Trachsel et al., 2013; dathe et al., 2016). Therefore, under the condition of limited resources, the depth and steep of maize root play an important role in nutrient utilization and yield formation. Hnammer (Haminer et al., 2009) found that the increase in maize yield and density tolerance in the United States in recent years was mainly due to the continuous optimization of root architecture by studying the maize shoot-root relationship. At the same time, breeders have also turned their attention to root research. Improving root traits and increasing density tolerance are the key points to achieving yield improvement. Promoting grain yield by improving root architecture is also known as the 'underground revolution' and 'second green revolution' (Lynch et al., 2007; hochholdinger et al., 2016). Therefore, genetic modifications of root traits provide an opportunity for maize grain yield improvement in high-density planting system.

Under supra-optimal planting population, competition for light reduces the whole plant photosynthesis and the generation of photoassimilates, and changes the relationship between the shoot and the root, together with the architecture of the plant (Poorter et al., 2016). It was found that during the breeding process, as the root expansion angle and the horizontal root distribution range decreased, the planting density increased. In the vertical direction, the root length density increased in the 0-20 cm soil layer. York believed that this was a manifestation of the increase in the number of root-adapted populations (York et al., 2015). Li found that the root distribution was closely related to the aboveground, showing significant genotypic differences, the root distribution of the flat-spike maize variety was shallower and more sensitive to the response of individual growth space limitation caused by densification; the compact nedium-spike maize varieties avoiding space limitation by narrowing the range of root horizontal expansion, increasing root growth in deep soil, and alleviating root accumulation in the plow layer. There are relatively few studies on the regulation of root angle-related proteins in maize, its application to crop improvement to increase density tolerance and increase yield has not been reported yet. Therefore, it is very important to explore the key genes of regulate root angle, and increase maize density tolerance to improve maize yield (Mi et al., 2016).

SUMMARY

The technical problem to be solved by the invention is how to regulate the density tolerance of plants.

To solve the above technical problems, the present invention provides any of the following applications of the ZmROA1 protein or substance regulating the content or activity of the ZmROA1 protein:

The application of I regulating plant root angle;

The application of U2 in preparation of products regulating plant root angle;

The application of U3 in regulating plant density tolerance;

The application of U4 in preparation of plant density-resistant products;

The application of U5 in plant breeding;

The ZmROA1 protein is the following A1, A2, or A3 protein:

A1, an amino acid sequence is the amino acid sequence shown in SEQ ID NO: 3;

A2, a protein, which is obtained by replacing and/or deleting and/or adding the amino acid sequence shown in SEQ ID NO: 3 through amino acid residues, is more than 80% identity to A1) and relates to plant root angle;

A3, a fusion protein is obtained by linking the N-end or/and C-end of A1) or A2) to protein tags.

Figure 10:
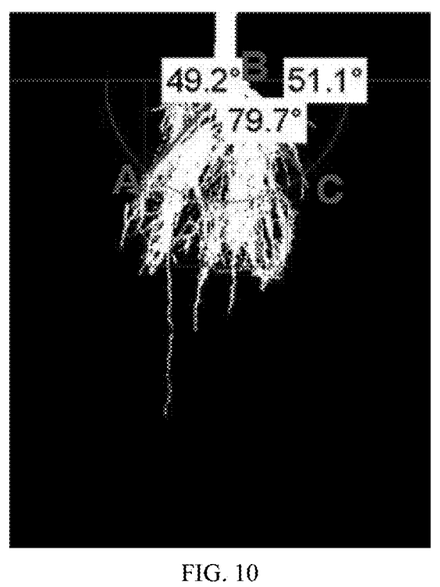
FIG. 10, a schematic diagram of the root angle of the invention. The <ABC is the root angle in the figure.

Root angle refers to the angle formed by the extension of the maize underground node roots (<ABC in FIG. 10).

In the above applications, SEQ ID NO: 3 in the sequence table is composed of 255 amino acid residues.

In the above applications, identity refers to the identity of amino acid sequences. Homology search sites on the Internet can be used to determine the identity of amino acid sequences, such as the BLAST page of the NCBI home page. For example, when using blastp as a program in advanced BLAST2.1, the identity of a pair of amino acid sequences is retrieved and calculated, and then the value of identity (%) is obtained by setting Expect value to 10 and all Filters to OFF, using BLOSUM62 as Matrix and setting Gap existence cost, Per residue gap cost and Lambda ratio to 11, 1 and 0.85 (default value) respectively.

In the above applications, the 80% identity mentioned above may be at least 81%, 85%, 90%, 91%, 92%, 95%, 96%, 98%, 99%, or 100% identity.

In the above applications, the ZmROA1 protein may be derived from maize.

In the above applications, the plant is a monocotyledonous plant or a dicotyledonous plant; furthermore, the monocotyledons are gramineous plants; furthermore, the gramineous plant is maize.

In the above applications, a substance that regulates the content or activity of the ZmROA1 protein can be at least one of the following six regulatory substances: B1) Regulation on the gene transcriptional level; B2) Regulation after transcription of the gene (i.e. regulation on splicing or processing of the genic primary transcripts); B3) Regulation on the genic RNA transport (i.e. regulation on the genic mRNA transport from the nucleus to the cytoplasm); B4) Regulation on the gene translation; B5) Regulation on the genic mRNA degradation; B6) Regulation after translation of the gene (i.e. regulation on the activity of the protein translated by the gene)

In the above applications, the substance that regulates the content or activity of the ZmROA1 protein is a biological material related to the ZmROA1 protein; the biological material is any of the following C1-C3:

C1, nucleic acid molecules that encode the ZmROA1 protein;

C2, nucleic acid molecules that increase the expression of ZmROA1 protein;

C3, expression cassettes, recombinant vectors, recombinant microorganisms, transgenic plant cell lines, transgenic plant tissues, or transgenic plant organs that contain nucleic acid molecules described in C1 or C2.

In the above applications, the nucleic acid molecules described in C1 or C2 can be DNA, such as cDNA, genomic DNA, or recombinant DNA; the nucleic acid molecules can also be RNA, such as mRNA or hnRNA.

In the above applications, the nucleic acid molecules described in C1 can be the following genes shown in D1 or D2:

D1, a coding sequence of coding chain is the 91-858$^{th}$ nucleic acid molecule of SEQ ID NO: 2 in the sequence table;

D2, nucleotide sequences are nucleic acid molecules of SEQ ID NO: 1 in the sequence table.

In the above applications, the substance that regulates the content or activity of the ZmROA1 protein can be achieved by increasing the content or activity of the ZmROA1 protein, specifically, it can be achieved by increasing the expression of the coding gene of the ZmROA1 protein, specifically, it can be achieved by W1 or W2:

W1 makes plants contain ZmROA1 gene;

W2 makes plants overexpress ZmROA1 gene.

The methods include but are not limited to the transgene, hybridization, backcross, selfing, or asexual reproduction.

In the above applications, the method of ZmROA1 gene overexpression is selected from one or more combinations of the following X1~X4:

X1, introducing plasmids including the ZmROA1 gene into a plant;

X2, increasing the copy number of ZmROA1 gene on plant chromosomes;

X3, replacing the promoter of the ZmROA1 gene with a strong promoter. In one embodiment of the invention, the ZmROA1 gene is overexpressed using the maize constitutive promoter Ubiquitin1.

The above import and replacement can be achieved by homologous recombination.

The invention also provides a protein named ZmROA1 protein, which is the following A1, A2 or A3 protein:

A1, the amino acid sequence is the amino acid sequence shown in SEQ ID NO: 3;

A2, the protein, which is obtained by replacing and/or deleting and/or adding the amino acid sequence shown in SEQ ID NO: 3 through amino acid residues, is more than 80% identity to A1) and relates to plant root angle;

A3, the fusion protein is obtained by linking the N-end or/and C-end of A1) or A2) to protein tags.

The invention also provides a biological material related to the ZmROA1 protein; the biological material is any of the following C1-C3:

C1, nucleic acid molecules that encode the ZmROA1 protein;

C2, nucleic acid molecules that increase the expression of ZmROA1 protein;

C3, expression cassettes, recombinant vectors, recombinant microorganisms, transgenic plant cell lines, transgenic plant tissues, or transgenic plant organs that contain nucleic acid molecules described in C1 or C2.

To solve the above-mention-ed technical problems, the invention provides plant reagents for increasing density tolerance and/or reducing root angle. The active ingredients of the plant reagents are substances that promote the expression of genes encoding the ZmROA1 protein and increase the abundance of the ZmROA1 protein. The active ingredients can be the ZmROA1 protein and/or the ZmROA1 protein-related biomaterial specifically.

The active ingredients of the plant reagents mentioned above that increase density tolerance and/or reduce root angle may also contain other biological or/and non-biological ingredients, and other active ingredients of the plant reagents mentioned above can be determined by technicians in this field according to the density tolerance and/or root angle effect of the plant.

To solve the above-mentioned technical problems, the invention also provides a method for improving the density tolerance of a plant and/or reducing the root angle of the plant, comprising the following steps: promoting the expression of the ZmROA1 protein in the receptor plant or increasing the abundance of the ZmROA1 protein to obtain a target plant having a density tolerance higher than and/or a root angle smaller than the receptor plant.

Wherein, the promotion of the expression of the ZmROA1 protein in the receptor plant or the increase of the abundance of the ZmROA1 protein may be achieved specifically by increasing the expression level of the gene encoding the ZmROA1 protein, specifically by the method of W1 or W2:

W1 makes plants contain ZmROA1 gene;

W2 makes plants overexpress ZmROA1 gene.

The methods include but are not limited to the transgene, hybridization, backcross, selfing, or asexual reproduction.

In the above applications, the method of ZmROA1 gene overexpression is selected from one or more combinations of the following X1-X4:

X1, introducing plasmids including the ZmROA1 gene into a plant;

X2, increasing the copy number of ZmROA1 gene on plant chromosomes;

X3, replacing the promoter of the ZmROA1 gene with a strong promoter. In one embodiment of the invention, the ZmROA1 gene is overexpressed using the maize constitutive promoter Ubiquitin1.

The above import and replacement can be achieved by homologous recombination.

The plant may be any of the following plants:
E1) Monocotyledonous plants,
E2) Cyperaceae plants.
E3) Gramineae.
E4) *Zea* plants.
E5) Maize.

In this invention, the regulation can be up-regulated or enhanced, or improved.

In the present invention, the purpose of plant breeding may include the cultivation of density-tolerant and/or angle-reducing plants.

The invention constructs a maize overexpression vector of ZmROA1. In the Optimal selection of embodiments, the main skeleton of the maize expression vector is composed of the promoter of the Ubiquitin1 gene from maize and the 3 transcription termination region from the carmine synthase (Trios) gene, and the selection marker gene is phosphinothricin. The expression vector is pBCXUN vector, and the recombinant plasmid pBCXUNA-ZmROA1 is constructed, in which the ZmROA1 gene is inserted in the forward direction and the expression is driven by the maize Ubiquitin1 promoter. In this invention, the overexpression vector containing ZmROA1 was transformed into maize inbred line B73-329, and the transgenic maize with reduced root angle and unaffected yield per plant was obtained. The invention uses transgenic maize overexpressing ZmROA1 gene to carry out different density experiments. The transgenic maize overexpressing ZmROA1 gene significantly reduced the root angle, enhanced the density tolerance, and increased the yield under high density.

Through the above technical solutions, the invention has at least the following advantages and beneficial effects: the invention discovers that the ZmROA1 gene has the biological function of regulating maize root angle and density tolerance for the first time. The expression of ZmROA1 regulation in maize can regulate the root angle of maize, ZmROA1 overexpression gene can decrease the root angle and improve the density tolerance of maize. The invention provides a new method to decrease the root angle of maize by using the ZmROA1 gene, which can be used for the cultivation of new varieties of density-tolerant maize, it is beneficial to the high and stable yield of maize and the improvement of maize harvest index.

BRIEF DESCRIPTION OF THE DRAWINGS

FIGS. 4A-4B, the gravitropism analysis results of the OE-ZmROA1(OE-ZmROA1-3, OE-ZmROA1-4) in embodiment 4 of the invention.

FIGS. 5A-5D, the field phenotypic results of overexpression ZmROA1 (OE-ZmROA1-3, OE-ZmROA1-4) in embodiment 5.

FIGS. 6A-6C. the root phenotypic of the density test for the overexpression ZmROA1 (OE-ZmROA1-3, OE-ZmROA1-4) in Embodiment 6. LD refers to the low density of 80000 plants/hectare, MD refers to the medium density of 120000 plants/hectare, and HD refers to the high density of 160000 plants/hectare.

FIG. 7B, the result of ear height under different densities. In the figures, * represents the difference significance analysis result P<0.05,  represents the difference significance analysis result P<0.01, and * represents the difference significance analysis result P3<0.001.

FIGS. 9A-9B, the yield result of the density test of the overexpression ZmROA1(OE-ZmROA1-3, OE-ZmROA1-4) in embodiment 6 of the invention.

DETAILED DESCRIPTION OF THE EMBODIMENTS

The invention is further described in detail in combination with the specific embodiments in the following, and the embodiments given are only for clarifying the invention, not for limiting the scope of the invention. The embodiments provided below can be used as guidelines for further improvements by ordinary technicians in this technical field and do not constitute a limitation on the invention in any way.

In the quantitative test of the following embodiments, three repeated experiments are set up and the results are averaged.

The experimental methods in the following embodiments are conventional unless otherwise specified. The materials, reagents, etc. used in the following embodiments can be obtained from commercial channels without special instructions.

The pBCXUN vector of the following embodiments is recorded in the non-patent literature 'Ya-Juan Qin, Wei-Hua Wu, and Yi Wang.ZmHAK5 and ZmHAK1 functions in K+ uptake and distribution in maize under low K-+ conditions. Journal of Integrative Plant Biology. June 2019. Volume 61, Issue 6,691-705', which is available to the public from China Agricultural University (i.e., the applicant) to repeat the application experiments and cannot be used for other purposes.

The maize inbred line B73 and B73-329 in the following embodiments are recorded in the non-patent literature 'Ya-Juan Qin, Wei-Hua Wu. ZmHAK5 and ZmHAK1 function in K+ uptake and distribution in maize under low K+ conditions. Journal of Integrative Plant Biology. June 2019, Volume 61, Issue 6,691-705', available to the public from China Agricultural University (i.e. the applicant) to repeat the application experiments and cannot be used for other purposes.

SIPSS18.0 statistical software was used to process the data in the following implementation cases, the experimental results are expressed as average value ±standard deviation using the T-test and Duncan test. * represents the significance analysis result is P<0.05,  represents the significance analysis result is P<0.01, * represents the significance analysis result is P<0,001, ns represents no significant difference.

Embodiment 1 Construction of Maize Transgenic Overexpression Lines

1. Cloning of Target Gene CDS

According to the genome sequence of ZmROA1 obtained by bioinformatics, as shown in SEQ ID No: 1, the 90th-96th is the first exon, the 216th-282rd is the second exon, the 2037th-2536th is the third exon, the 2634th-2808th is the fourth exon, and the 2926th-2945th is the fifth exon. The cDNA sequence of ZmROA1 is shown in SEQ ID No: 2 (the 5UTR region is at positions 1st-90th, the CDS region is at positions 91st-858th, and the 3'UTR region is at positions 859th-1014th), and its encoded amino acid sequence is shown in SEQ ID No: 3.

Primers design: The primer pair for amplifying ZmROA1 consists of forward primer ZmROA1-F and reverse primer ZmROA1-R. ZmROA1-F contains the translation initial codon ATG, and the reverse primer ZmROA1-R contains the reverse complementary sequence of the translation terminator codon TAA.

ZmROA1-F:
5'-<u>ATG</u>AAGATTTTCAGTTGGGT-
3', as shown in SEQ ID NO: 4
(the underlined sequence is the start codon ATG);

ZmROA1-R:
5'-<u>TTA</u>CATTTCGAGCACAATAA-
3', as shown in SEQ ID NO: 5
(the underlined sequence indicates the reverse complementary sequence of the translation termintor codon TAA).

The open reading frame of ZmROA1 was amplified using the cDNA of B73 maize root by using the KOD DNA Polymerase (New England Biolabs, Ipswich, MA, USA).

The amplification system is shown in Table 1:

TABLE 1

| Amplification System | |
|---|---|
| Reagent name | Volume |
| 2 × PCR Buffer for KOD FX | 25 μL |
| 2 mM dNTPs | 10 μL |
| Forward primer(10 μM) | 1 μL |
| Reverse primer(10 μM) | 1 μL |
| KOD DNA Polymerase | 1 μL |
| cDNA | 1 μL |
| ddH$_2$O | 11 μL |
| Total | 50 μL |

The PCR cycling parameters is shown in Table 2

TABLE 2

| PCR reaction procedure | | |
|---|---|---|
| Temperature | Time | cycles |
| 94° C. | 2 min | |
| 98° C. | 10 sec. | |
| 60° C. | 30 sec. | 25-40 cycles |
| 68° C. | 30 sec./kb | |
| 68° C. | 7 min | |

PCR product recycle: Detect 5 μl PCR products on 1.0% agarose gel electrophoresis, and the PCR product can be directly recycled and purified by the E.Z.N.A. Cycle Pure Ki (E.Z.N.A. Cycle Pure Kit, OMEGA). The test method refers to the instructions of the kit, the recycled product contains the sequence shown at position 91-858 of SEQ ID No: 2.

2. Construction of Plant Expression Vector

Figure 1:
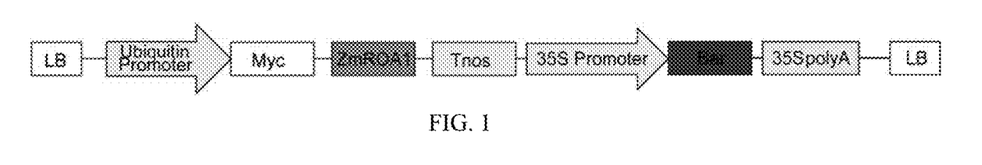
FIG. 1, a skeleton of the ZmROA1 overexpression vector constructed in embodiment 1. of the invention. Among them, the ZmUbiquitin1 was used as the promoter, and the promoter was followed by a ye tag, the Tnos was used as the terminator, and ZmROA1 is between the Myc tag and the terminator.
Figure 2A:
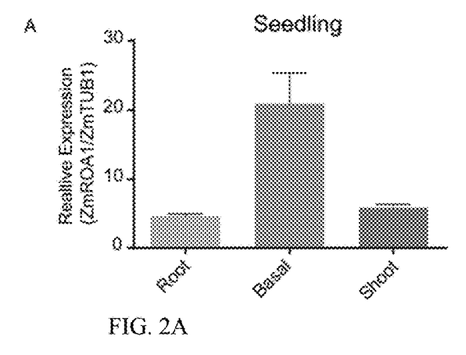
FIGS. 2A-2D, the spatial-temporal expression pattern of ZmROA1 in embodiment 2 of the invention. The relative expression of ZmROA1 in different tissues, including root tips(Tip), crown root(Root), above root (Above Root), basal, stem and leaf at seedling stage (FIG. 2A), jointing stage (FIG. 2B), silking stage (FIG. 2C), and 15 days after pollination(DAP15, FIG. 2D). ZmTUB1 was used as the reference transcript.
Figure 2B:
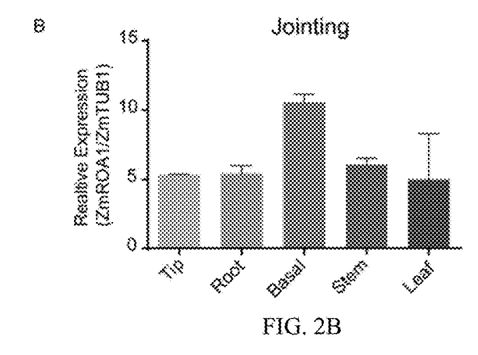
Figure 2C:
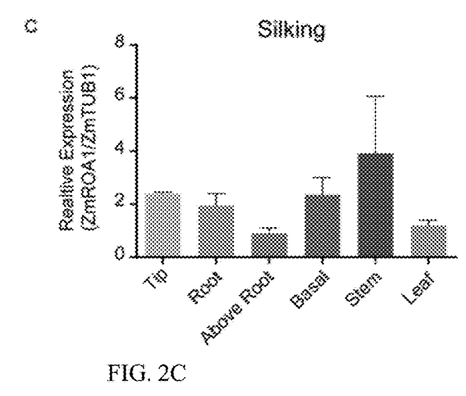
Figure 2D:
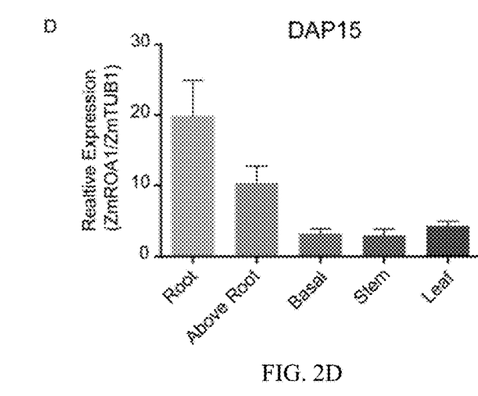

The expression vector used in the experiment is pBCXU N. The vector skeleton is shown in FIG. 1. The main skeleton contains the promoter of the Ubiquitin1 gene from maize and the 3' transcription termination region from the carmine synthase (Tnos) gene. The selection marker gene is phosphinothricin. The pBCXUN vector was obtained from the Center for Crop Functional Genomics and Molecular Breeding of China Agricultural University.

The pBCXUCN vector was digested by the XcmI enzyme (purchased from Beijing Friendship Zhonglian Biotechnology Co., Ltd.) to obtain a linearized vector. The digestion system was: 10×NEB buffer 5 μL; Carrier: 2 μL; XcmI restriction enzyme 1 μL; ddH2O 42 μL; Incubation temperature: 37° C.; Incubation time: 6 hours.

The recycled product was used as the template for further PCR amplification with a new primer carrying the homologous arm of the pBCXUN vector (the forward primer of the ligation vector was ZmROA1-infusion-F, and the reverse primer of the ligation vector was ZmROA1-infusion-R). The vector was constructed using the method of infusion (SE seamless cloning and assembly kit catalog number: ZC231). Specific primers and methods are as follows:

ZmROA1-infusion-F:
5'-AGATCTTCCAATACTAATGAAGATTTTTTCAGTTGGGT-3',
as shown in SEQ ID NO: 6 (the sequence indicated
by the underline is the homologous arm sequence
of pBCXUN vector);

ZmROA1-infusion-R:
5'-CGGATCCCCAATACTTTACATTTCGAGCACAATAA-3',
as shown in SEQ ID NO: 7 (the sequence
indicated by the underline is the homologous arm
sequence of the pBCXUN vector).

The reaction system is shown in Table 3

TABLE 3

Reaction system

| Reagent name | Volume |
| --- | --- |
| 5 × SE Cloning Buffer | 2 µL |
| Linearized carrier | 3 µL |
| insertion fragment | 2 µL |
| SE Recombinase | 1 µL |
| ddH$_2$O | Supplement to total volume 10 µL |

After mixing in a 37° C. water bath or PCR reaction for 5-30 minutes, Transfer it to ice or −200° C. and then store it.

The pBCXUN-ZmROA1 containing the ZmROA1 gene (nucleotides are shown at position 91-858 of SEQ ID No: 2). The ZmROA1 gene was inserted between the XcmI restriction sites and driven by the maize Ubiquitin1 promoter.

In the construction of recombinant expression vector pBCXUNT-ZmROA1, the CDS region of the ZmROA1 gene shown in SEQ 1D No: 2.91-858 can also be artificially synthesized.

3. Competence Transformation:

Using the recombinant expression vector pBCXUN-ZmROA1 to transform competent cells TOPIC (purchased from Beijing Biomed Technology Co., Ltd.), and then screened by LB plate containing Kanamycin. 3-5 clones were selected for sequencing, and the correct recombinant plasmid was obtained (containing the nucleotide sequence shown at position 91st-858th of SEQ TD No: 2).

4, Maize Genetic Transformation

The correct recombinant plasmid was transformed into Agrobacteriuin *tumefaciens* EHA105 by electroporation. The positive single colonies were identified as recombinant Agrobacteriun tumefaciens EHA105-ZmROA1 by colony PCR. The recombinant Agrobacterium EHA105-ZmROA1 carrying the target gene was used to transform the immature embryos of maize inbred line B73-329, and several single-copy homozygous positive seedlings were obtained after screening. This step was assisted by the Crop Functional Genomics and Molecular Breeding Research Center of China Agricultural University.

The single copy homozygous positive seedlings mentioned above were transgenic plants (TO generation) with overexpressing ZmROA1 gene generated by strong promoter Ubiquitin1. Each transgenic plant (TO generation) was self-bred to obtain four lines, named OE-ZmROA1-1, OE-ZmROA1-2, OE-ZmROA1-3, and OE-ZmROA1-4.

Embodiment 2 Spatial-Temporal Expression Pattern Analysis of ZmROA1

We subsequently assessed the expression of the ZmROA1 at four different developmental stages (seedling, jointing, silking, and 15 days after pollination stages) using the inbred line B73-329. The root tips, crown roots, above roots, basals, stems, and leaves were taken from each stage. After sampling, they were wrapped with tin foil paper and quickly stored in liquid nitrogen. The tissues were ground by mortar and the total RNA of maize was extracted by RNAiso Plus Kit (Takara) and the cDNA was generated using the Prime Script RT reagent Kit (Takara). The maize ZmROA1 gene was amplified by real-time PCR with primers ZmROA1 qPCR-F and ZmROA1 qPCR-R. A maize gene ZmTUB1 was used as the internal control for normalizing gene expression. And the ZmTUB1 gene of maize was amplified with primers ZmTUB1 qPCR-F and ZmTUB1 qPCR-R.

ZmROA1qPCR-F:
5'-GGAAAGAGCATGACGGTGAA-3',
as shown in SEQ ID NO: 8;

ZmROA1qPCR-R:
5'-GCAGTCTAAGGAGCGAGGC-3',
as shown in SEQ ID NO: 9;

ZmTUB1qPCR-F:
5'-GCTATCCTGTGATCTGCCCTGA-3',
as shown in SEQ ID NO: 10;

ZmTUB1qPCR-R:
5'-CGCCAAACTTAATAACCCAGTA-3',
as shown in SEQ ID NO: 11.

As shown in FIGS. 2A-2D, ZmROA1 was expressed in the seedling stage (FIG. 2A), jointing stage (FIG. 2B), silking stage (FIG. 2C), 15 days after pollination (FIG. 2D) and various tissues of maize. The expression pattern was a constitutive expression, and it was highly expressed in roots compared with other parts. Among them, the expression level was the highest at the basal of the seedling (FIG. 2A) and jointing stages (FIG. 2B), which was the key part of maize crown root formation. It shows that ZmROA1 plays a key role in regulating the root angle.

Embodiment 3 Expression Analysis of Overexpression ZmROA1

Maize inbred line B73-329 (wild type) and OE-ZmROA1 (T2 plants of 4 independent transgenic lines of OE-ZmROA1-1, OE-ZmROA1-2, OE-ZmROA1-3, OE-ZmROA1-4 obtained from embodiment 1) were first cultured in ½ Hoagland nutrient solution for 3 days, then cultured in normal nutrient solution for 14 days, and the culture solution was renewed every 3 days. The whole root system of maize was taken, and every 3 plants were mixed for one sample, with 3 biological replicates.

Total RNA was extracted from plant samples using RNAiso Plus Kit (Takara). The cDNA was generated using the Prime Script RT reagent Kit (Takara). Real-time PCR was used to amplify the ZmROA1 gene of maize with primers ZmROA1 qPCR-F and ZmROA1 qPCR-R. A maize gene ZmTUB1 was used as the internal control for normalizing gene expression. And the ZmTUB1 gene of maize was amplified with primers ZmTUB1 qPCR-F and ZmTUB1 qPCR-R.

ZmROA1qPCR-F:
5'-GGAAAGAGCATGACGGTGAA-3', as shown in SEQ ID NO: 8

```
-continued
ZmROA1qPCR-R:
5'-GCAGTCTAAGGAGCGAGGC-3', as shown in SEQ ID NO: 9

ZmTUB1qPCR-F:
5'-GCTATCCTGTGATCTGCCCTGA-3', as shown in SEQ ID NO: 10

ZmTUB1qPCR-F:
5'-CGCCAAACTTAATAACCCAGTA-3', as shown in SEQ ID NO: 11
```

Figure 3:
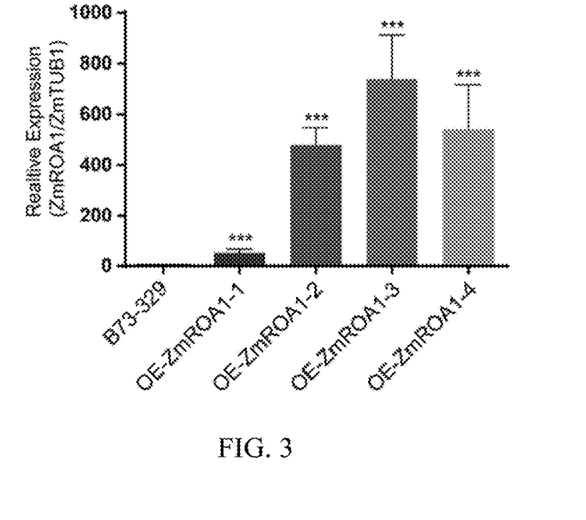
FIG. 3, the quantification result of the ZmROA1 expression level in different transgenic overexpression lines in embodiment 3 of the invention. In the figure, *** represents the difference significance analysis result is P<O001.

The results are shown in FIG. 3, to test whether elevated expression of ZmROA1 could regulate maize root angle, we generated four independent transgenic lines (OE-ZmROA1-1, OE-ZmROA1-2, OE-ZmROA1-3 and OE-ZmROA1-4) by overexpressing ZmROA1 under the control of the maize Ubiquitin promoter. In these four transgenic lines, the transcript levels of ZmROA1 were significantly increased up to 10 to 800 folds of that in the WT. among which the expression level of the OE-ZmROA1-3 line was the highest, followed by the OE-ZmROA1-4 line. According to the expression level, OE-ZmROA1-3 and OE-ZmROA1-4 were selected as the follow-up research objects to experiment.

Embodiment 4 Gravitropism Analysis of ZmROA1

The ½ MS Solid Medium (pH=5.8) was Prepared as Follows:

TABLE 4

| Formulation of ½MS solid medium | |
| --- | --- |
| Reagent name | Quantity |
| MS basal salt(phytotech) | 2.165 g |
| Phytagel | 10 g |
| Sucrose | 15 g |
| ddH$_2$O | 1 L |
| Total | 1 L |

According to Table 4, each component was fully dissolved and adjusted to pH 5.8 with a 5 M NaOH solution. Autoclaving at 121° C. for 20 min.

The seeds of T2 generation of maize inbred line B73-329 and OE-ZmROA1-3, OE-ZmROA1-4 were disinfected with 2% sodium hypochlorite for 30 minutes, rinsed with 70% alcohol for 5-10 seconds, and then rinsed with sterilized ddH2O vortex for 6 times with 1 minute for each time. The sterilized seeds were seeded in ½MS solid medium and grown in darkness at 28° C. The 3-day-old seedlings were placed on 1NO agar in normal condition for 12 h, and then were placed horizontally. The primary root curvature was defined as the angle formed between the growing direction of the apex and the horizontal base line and was measured after 24 hours.

Figure 4A:
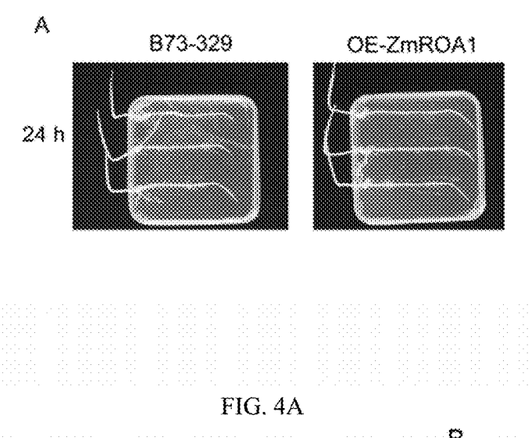
FIG. 4A, a phenotype of the root gravity response after 24 hours.
Figure 4B:
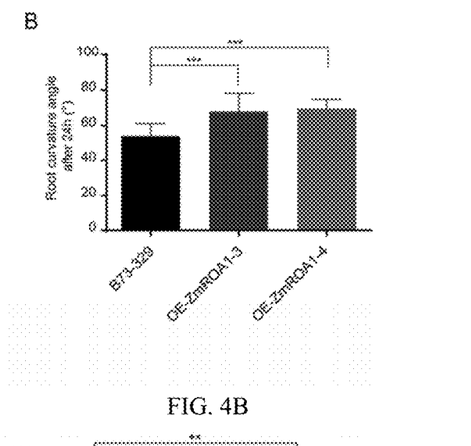
FIG. 4B, the statistical results of the root curvature angle after 24 hours. In the figures, ***represents the difference significance analysis result is P<0.001.

As shown in FIGS. 4A-4B, the gravity bending angle of OE-ZmROA1(OE-ZmROA1-3, OE-ZmROA1-4) was significantly higher than that of the wild type after 24 hours of bending, indicating that ZmROA1 affected the change of maize root angle through gravity reaction. Therefore, we provide a line of evidence to maize that ZmROA1 acts as a major component of this gravity pathway.

Embodiment 5 Functional verification of ZmROA1 gene under field conditions

Experimental design: The study was conducted in Hainan, China, in 2020 and in Beijing, China, in 2021. The experimental materials were two transgenic overexpression lines (T2 generation plants of OE-ZmROA1-3 and OE-ZmROA1-4 lines in implementation 1) and wild-type (B73-329). The maize plants were evaluated in a completely randomized block design of one-row plots with three replications. Each row contained 17 plants with 0.5 m inter-row spacing and 0.25 m intra-row spacing. Standard cultivation management practices were used. Root system architecture traits were measured at silking stage.

Figure 5A:
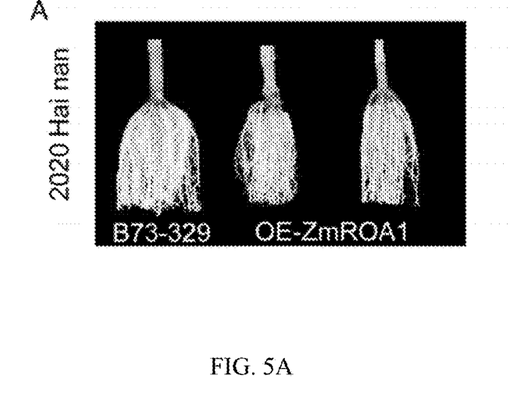
FIG. 5A, the root phenotype results of overexpression ZmROA1 (OE-ZmROA1-3, OE-ZmROA1-4 are marked as OE-ZmROA1) in Sanya, lainanin 2020, FIG. 5B, the root phenotype results of overexpression ZmROA1 (OE-ZmROA1-3, OE-ZmROA1-4) in Sanva. Hainanin 2020.
Figure 5B:
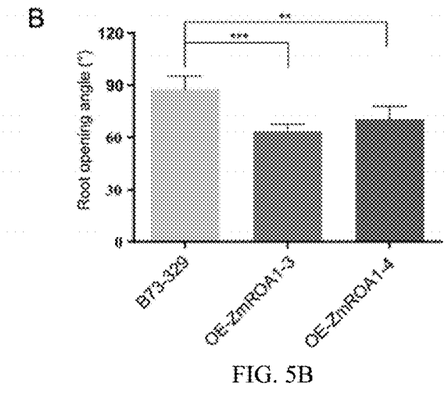
Figure 5C:
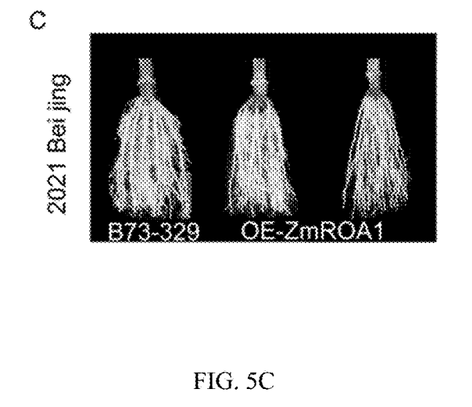
FIG. 5C, the root phenotype result of overexpression ZmROA1 (OE-ZmROA1-3, OE-ZmROA1-4 are marked as OE-ZmROA1) in Shangzhuang, Beijing in 2021.
Figure 5D:
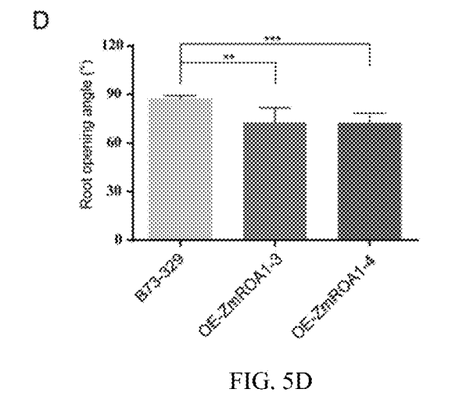
FIG. 5D, the root phenotype result of overexpression ZmROA1 (OE-ZmROA1-3, OE-ZmROA1-4) in Shangzhuang, Beijing in 2021. In the Figures,  represents the difference significance analysis result P<0,01, and * represents the difference significance analysis result P<0.001.

The results are shown in FIGS. 5A-5D: We verified the function of the ZmROA1 regulated maize root angle of field grown maize at silking stage during 2 years (2020 and 2021). It was found that the root angle of the overexpressed ZmROA1 was significantly reduced compared to the wild type, and the results were highly consistent in two years. In 2020, the average angle of wild-type B73-329 was 87.42°, the average angle of OE-ZmROA1-3 was 72.78°, and the average angle of OE-ZmROA1-4 was 72.33°. Compared with the wild type, the angles were reduced by 16.76% and 17.27%, respectively (FIG. 5A, FIG. 5B). In 2021, the average angle of the wild type is 79.58°, the average angle of OE-ZmROA1-3 is 66.22°, compared with the wild type, the angle was reduced by 16,79% and 27.84%, respectively (FIG. 5C, FIG. 5D). Therefore, it is proved that ZmROA1 has the function of regulating maize root angle.

Embodiment 6 Field Density Trial of ZmROA1 Overexpression

Experimental design: The study was conducted in Beijing, China, in 2021. The experimental materials were two transformation events of overexpression of ZmROA1(T2 generation plants of OE-ZmROA1-3 and OE-ZmROA1-4 lines in embodiment 1) and wild type B73-329. The experiments were a split-plot design with three replicates (blocks), with planting density as the main plots, genotypes as subplots. Three planting densities were imposed, that is, 80000, 120000 and 160000 plants ha$^{-1}$, which are abbreviated as LD (low density), MD (medium density) and HD (high density), respectively. The row widths were 0.6 m for all the three density treatments. The row lengths were 4.0 in for all the three density treatments. The plots were thinned to the designed planting density at V3 stage. Weeds in the plots were controlled using herbicides (atrazine and acetochlor). Pesticides were applied as needed to control insect populations. Plant height, ear height, and root architecture-related traits were measured at the silking stage. The yield was measured at the mature stage.

Figure 6A:
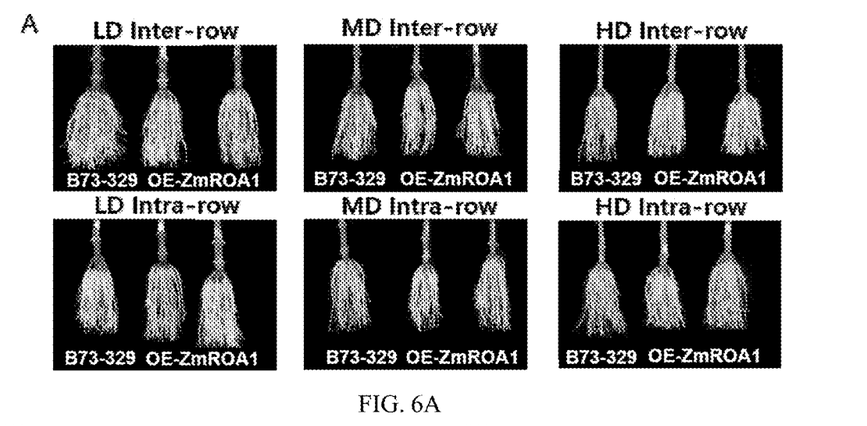
FIG. 6A, the picture of the root angle between inter-row and intra-row under different densities, FIG. 6B, the root angle in inter-row direction under different densities.
Figure 6B:
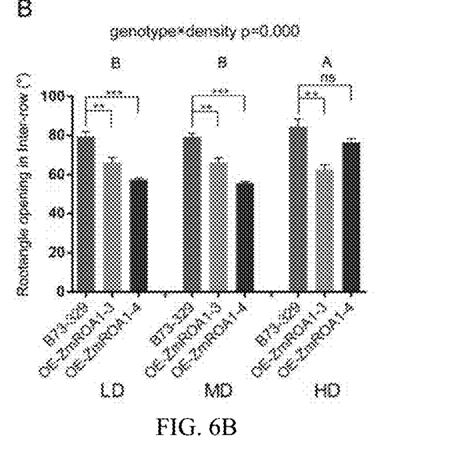
Figure 6C:
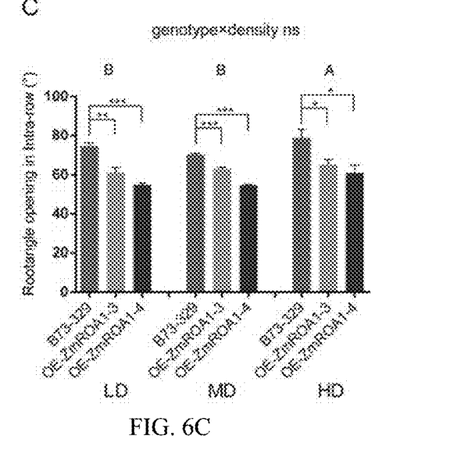
FIG. 6C, the root angle in intra-row direction under different densities. In the figures, ns represents no significant difference, * represents the difference significance analysis result is P<0.05,  represents the difference significance analysis result is P<0.01, and * represents the difference significance analysis result is P<0.001.

The results of the experiment are shown in FIGS. 6A-6C: The study found that Overexpression lines OE-ZmROA1-3 and OE-ZmROA1-4 showed a significant reduction in root angle, compared with WT (B753-329) at the same density (FIG. 6A). Root angles in inter-row direction was significant interaction between the density and the genotype. (FIG. 6B), and no interaction between the intra-row and the genotype (FIG. 6C). We found no significant differences between intra-row root angle and inter-row root angle at the LD However, with increasing plant density, the root angle significantly increased in the inter-row direction for WT plants, and there was no difference for overexpression lines. It shows that the overexpression root architecture has sufficient living space and does not need to make adaptive changes. The root angle decreases and the root system is tied down, which is beneficial for the plant to reduce the lateral nutrient competition pressure and absorb the deep soil nutrients under high density conditions.

Figure 7A:
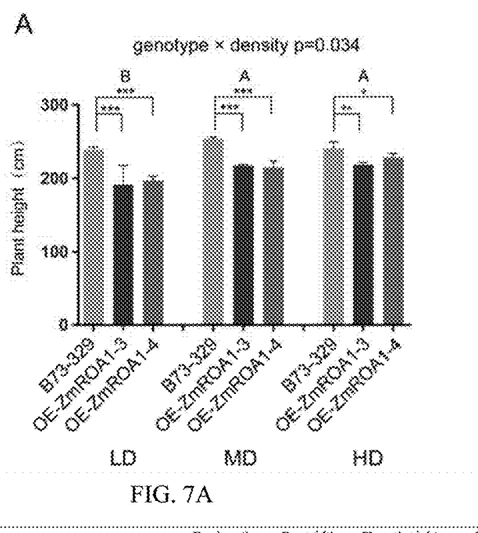
FIGS. 7A-7B, the results of plant height and ear height of the density test for the overexpression ZmROA1(OE-ZmROA1-3, OE-ZmROA1-4) in embodiment 6 of the invention, FIG. 7A, the result of plant height under different densities.
Figure 7B:
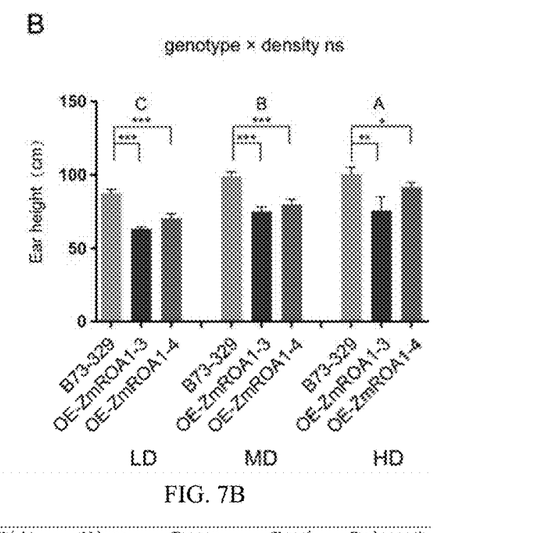

For plant height (FIG. 7A), there was a significant interaction between genotype and density. Compared to LD, plant height at MD and HD was much affected, The plant height of the wild type was inhibited under HD, while the plant height of the ZmROA1 overexpression lines increased under HI. The plant height of OE-ZmROA1-3 and OE-ZmROA11-4 was significantly lower than wild type in the same density. The ear height was consistent with plant height, but there was no interaction between genotype and density (FIG. 7B). In conclusion, with the increase of density, the appropriate reduction of plant height and ear height can increase the lodging resistance of crops and play an important role in improving the density tolerance of maize.

Figure 8:
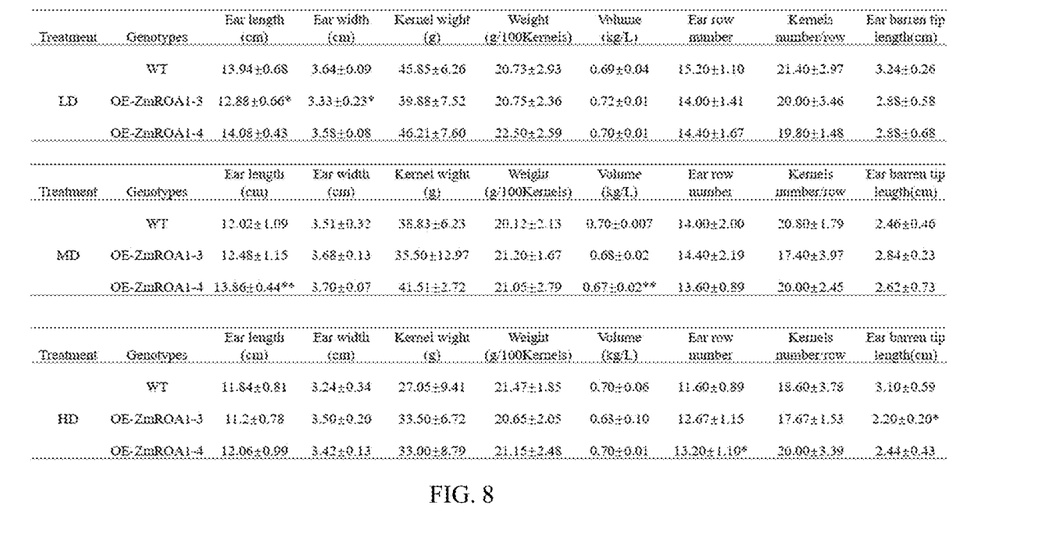
FIG. 8, the yield traits of overexpression ZmROA1(OE-ZmROA1-3, OE-ZmROA1-4) under different densities in embodiment 6 of the invention.

As shown in FIG. 8, the data analysis results showed that under LD, the ear length and ear width of OE-ZmROA1-3 decreased significantly compared with the WT, but there was no significant difference in kernels weight, 100-kernels weight, ear row number, kernels number per row and ear barren tip length. The OE-ZmROA1-4 was not significantly different from those of WT, indicating that the ZmROA1 overexpression lines did not affect the yield per plant of maize. Under the condition of MD, the ear length of OE-ZmROA1-4 was significantly longer than WT, but the volume weight was significantly lower than WT. Under HD conditions, the ear row number of OE-ZmROA1-4 was significantly higher than WT, and the ear barren tip length of OE-ZmROA1-3 was significantly reduced. There was no significant difference in other yield traits between wild-type and overexpression lines. The data shown in the figure are: means±standard deviation, T-test: * $P<0.05$,  $P<:0.01$, * $P<0.001$.

Figure 9A:
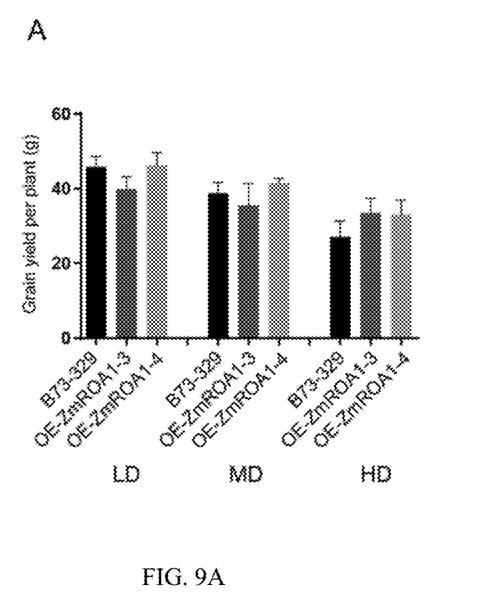
FIG. 9A, the yield per plant of maize under different densities.
Figure 9B:
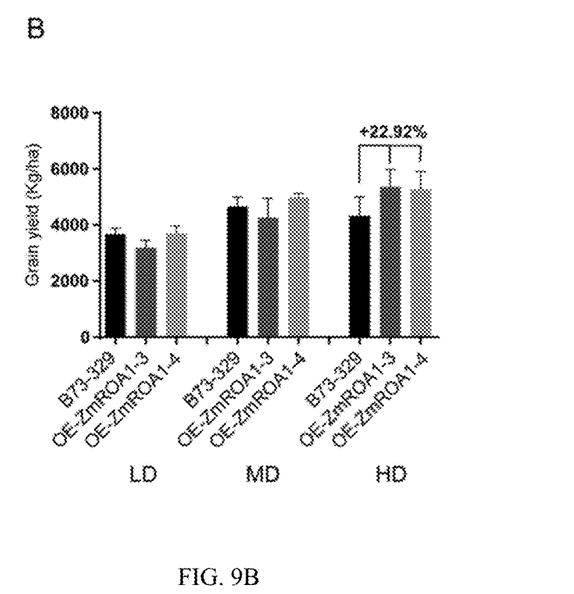
FIG. 9B, the yield at different densities.

We subsequently assessed the contribution of the ZmROA1 regulated root angle to yield of field-grown maize at maturation stages in three densities. (FIGS. 9A-9B), It can be concluded that although ZmROA1 overexpression lines can reduce the root angle and plant height, the yield per plant is not affected (FIG. 9A). With the increase of density, for WT plants, the yield reduction ranged from 15%-30%, while the yield reduction of overexpression ZmROA1 was only 5%-20%. Under high density, the overall yield of OE-ZmROA1-3 and OE-ZmROA1-4 increased by 22.92% on average (FIG. 9B) compared with the WT. In summary, with the increase of density, the yield of overexpression ZmROA1 has an increasing trend compared with WT. Our research demonstrated that ZmROA1 regulated root angle contributed substantially to overall yield under high planting system. And has a good application prospect in maize density tolerance and yield increase.

The above content describes the invention in detail. For technicians in this field, the invention can be implemented in a wide range under the same parameters, concentrations, and conditions without deviating from the purpose and scope of the invention and without unnecessary experiments. Although the invention gives special embodiments, it should be understood that the invention can be further improved. In short, following the principles of this invention, this application is intended to include any changes, uses, or improvements to this invention, including, changes made with conventional techniques known in this field, outside the scope disclosed in this application. Some basic characteristics can be applied according to the scope of the claims attached below

What is claimed is:

1. A method of increasing maize density tolerance, comprising a step of increasing an abundance of a ZmROA1 protein in a maize plant by overexpression of a gene encoding the ZmROA1 protein, wherein a ZmROA1 protein overexpressed has the amino acid sequence shown in SEQ ID NO: 3, and the ZmROA1 protein overexpression comprises inserting a gene encoding the ZmROA1 protein comprising the nucleotide sequence shown in SEQ ID NO: 1 between two XcmI restriction sites of a pBCXUN expression vector comprising a promoter of the Ubiquitin1 gene; transforming an immature maize plant embryo; expressing the recombinant ZmROA1 gene; producing overexpression maize lines and selecting a transformed maize plant from the overexpression maize lines that exhibits a reduced root angle, improved density tolerance, reduced plant height, and reduced ear height as compared to control maize plant not comprising said overexpression of the recombinant ZmROA1 gene.

* * * * *

SEQUENCE LISTING

```
Sequence total quantity: 11
SEQ ID NO: 1            moltype = DNA  length = 3101
FEATURE                 Location/Qualifiers
source                  1..3101
                        mol_type = other DNA
                        organism = Zea mays
SEQUENCE: 1
gtaggctagg ctcgcgctcc ctcatcccac tcccacgcac gtgtactact ttacttactg   60
gtgggggggcc ggtctccagt tccgcaggat atgaaggtgt gtgtgtgtgt gtgtctgaaa  120
ggcatagcat agcaagagta ctcctccttc gcctgacggc ggttggttgt ttcttcgatc  180
ctgacagcga attccctctc ttctccctcc cgcagatttt cagttgggta gccaacaaga  240
tcggcgggaa gcaagaaccg aagcgatctg ccgcgcatta tcgtaagcct acttcgcgcc  300
aatatttcac ttcattcctt ggcctgtgaa ttcagggtca aggtttttata tttcaagttg  360
aactttcttt tttttttctct ctctctcgtg aatctctctg tcctttgtat caactcctta  420
gtctctctat actactatct ccttgcatgc atgaatgtac ataaatatct ctgataagta  480
ctgtatccta gtattgatta cttttttgcat ggctgaggcg catcaaaatc accgcttttt  540
ctcggaggtg aatgatgccc cactccaccc cctcccctta atgagtgcag gtgaatagga  600
gggtctcgtt tgtttgggat aggtctagct tttttagcttc tccgaagaga atcacttcaa  660
ttccaacccg cagccaacac actcaactga tccaccctgt tttcgttcta ctatatattg  720
tggtgcgaat cacgagggaa tcaattctca tcagctcgta actctgctcc cctcctaaaa  780
atctactgga aacactccat caaagagcac agttgaagga ttaggaagcg gaggtctcca  840
aacggtgcct aaggtcgtgt ttgtttccct ccttggatta tggtaaaaaa gtaagatagt  900
caaatactct cttcgttttt ttatagttga cgatggttag tgtaaaattg cactagctaa  960
cctcaattta aaaaaataga ggtagtatca cttttcaaat tacaaatagg ctgaaataac 1020
ttaccccaac aatgcttata tatatatata tatatatata tatatatata tatatatatg 1080
gtgtcaaagt gatattttat cctcgtatct ttcatcacaa tccaacttat ataatatatg 1140
agagaaacaa gcacaccctaa agatgataga cctgggactt tgagtctgct tcttgcattc 1200
acgttctgct tcagtactct attcttcgtt tcagcatatc tttaactcta tatgctcctc 1260
ggaagggtgt gattatttag caagttctta taagttctct ttttgaagca aaagaaaagg 1320
agaagatagt tcttttcggc aatgcttgta tcagtttgga tggttcagtc ctactctcct 1380
atctgtcaac actgatatgt tcacaaatat ctttcaataa tctgctaagg aaatatgttt 1440
attatatcgc attttgatgc atgagagcac tacagtatcc cttcattttt ctttgcatat 1500
actgtacacg gtgtttttca atgactaaaa acctttttctt tcagccccctt gaacgagagt 1560
gtggtgaggt tcttatatga cacaaactgt ccagcggccg agttacattt gtaacgcaga 1620
atcgtaacct cggacggttc cgtactggat catcagatct gaagcacagt agatcatttc 1680
tctgtgttct ttattgttct tagaaaggct agaggggtag ggtggtaaca aacatcttcg 1740
gatgccgttg tgcgatagat taggtgatta tcagcatgat gtttcaggtt ggcgcgaaac 1800
atcgtggtgt ggagcaagca tgggcaaaca tgtttctcgt cagtgatagg ctgcaggctg 1860
```

```
ctgcatgcat gctcgatcat gaaaagcagc agcgatttaa aactgccaaa aattagtggt    1920
ccatacggcc gccgatttat gctaatatat tcacgtagta ggagtagggc catgattttt    1980
tttttttgttt ctttgtactg atttggccaa ctaattaatt tacttgcaac gcgcaggtgg   2040
caacgtatca gaatgtcgca acgacgagtt cagtgattgg ccccaatcat tgctggcaat    2100
cgggacgttt gggaacaggc agctggagga aggggtggtg gagacgtctt ctggaaacgt    2160
ccaggccgcg caagaccccg ccaagttcac agaggaagaa gaggcggaca gcatacggag    2220
agaactcgag gtgctgctgc tgcaaggcaa taataataat ggcggccaag cagaggcgca    2280
gggctctcgt ggagacgaac gacgacaggt agcttggaaa gagcatgacg gtgaatgtag    2340
caaggagaag cagccgacga gcggggagat ggtcacgacg aaggcgagag cgagagaaat    2400
ggtagcaggg aagaaaagga gcacgctgaa gccaaggtcg gtggcctcgc tccttagact    2460
gctcgcgtgc aagggcggct tgccacccc ggttctggaa ccgaggagcc ctttccccca    2520
gtcgagaatg gagaaggtac agtttcttgt actatagatt cgcacggctt cttctttctc    2580
tgcatctcgt tcacgtactt tgcgcgtggt tggtttggtc accgctgctg cagctgctca    2640
aggcgatact ggagaagaag atacacccgc agaacccag gcggctgca gcgaggcggc     2700
accagctgga ctggaagcta gacgagaaag agatcgacga gtgccttgac gacgcgctgc    2760
gtgacctcga cgacgacggc gccaagtggg tcaaaactga ctcggactgt aagtactact    2820
gtagaatgta gatcggcagc gaaactgcat gcacttcgtg tctatctatc tgacatgaga    2880
ctgaattcgt gtcctctttc ttgttttttct tttctttct ttcagttatt gtgctcgaaa    2940
tgtaaaggcc cgcgcgtgtg tggttatgtt tgtttctttg aggccaggta cgcacttctc    3000
gcctcttctg aaccctgga actttcaggt tcatatcatc agttgatctc agcgcgggta    3060
cgtctttcgt ttgatcagtt gttggtttat tggatgctca g                       3101

SEQ ID NO: 2              moltype = DNA  length = 1014
FEATURE                   Location/Qualifiers
misc_feature              1..1014
                          note = The sequence is synthesized.
source                    1..1014
                          mol_type = other DNA
                          organism = synthetic construct
SEQUENCE: 2
gtaggctagg ctcgcgctcc ctcatcccac tccacgcac gtgtactact ttacttactg    60
gtggggggcc ggtctccagt tccgcaggat atgaagattt tcagttgggt agccaacaag    120
atcggcggga agcaagaacc gaagcgatct gccgcgcatt atcgtggcaa cgtatcagaa    180
tgtcgcaacg acgagttcag tgattggccc caatcattgc tggcaatcgg gacgtttggg    240
aacaggcagc tggaggaagg ggtggtggag acgtcttctg gaacgtcca ggccgcgcaa     300
gaccccgcca agttcacaga ggaagaagag gcggacagca tacggagaga actcgaggtg    360
ctgctgctgc aaggcaataa taataatggc ggccaagcag aggcgcaggg ctctcgtgga    420
gacgaacgac gacaggtagc ttggaaagag catgacggtg aatgtagcaa ggagaagcag    480
ccgacgagcg gggagatggt cacgacgaag gcgagagcga gagaaatggt agcagggagg    540
aaaaggagca cgctgaagcc aaggtcggtg gcctcgctcc ttagactgct cgcgtgcaag    600
ggcggctttg ccacccggt tctggaaccg aggagcccctt tcccccagtc gagaatggag     660
aagctgctca aggcgatact ggagaagaag atacacccgc agaacccag cacggctgca    720
gcgaggcggc accagctgga ctggaagcta gacgagaaag agatcgacga gtgccttgac    780
gacgcgctgc gtgacctcga cgacgacggc gccaagtggg tcaaaactga ctcggacttt    840
attgtgctcg aaatgtaaag gcccgcgcgt gtgtggttat gtttgtttct tgaggccag     900
gtacgcactt ctcgcctctt ctgaaccct ggaactttca ggttcatatc atcagttgat     960
ctcagcgcgg gtacgtcttt cgtttgatca gttgttggtt tattggatgc tcag         1014

SEQ ID NO: 3              moltype = AA  length = 255
FEATURE                   Location/Qualifiers
REGION                    1..255
                          note = The sequence is synthesized.
source                    1..255
                          mol_type = protein
                          organism = synthetic construct
SEQUENCE: 3
MKIFSWVANK IGGKQEPKRS AAHYRGNVSE CRNDEFSDWP QSLLAIGTFG NRQLEEGVVE    60
TSSGNVQAAQ DPAKFTEEEE ADSIRRELEV LLLQGNNNNG GQAEAQGSRG DERRQVAWKE    120
HDGECSKEKQ PTSGEMVTSK ARAREMVAGK KRSTLKPRSV ASLLRLLACK GGFATPVLEP    180
RSPFPQSRME KLLKAILEKK IHPQNPSTAA ARRHQLDWKL DEKEIDECLD DALRDLDDDG    240
AKWVKTDSDF IVLEM                                                    255

SEQ ID NO: 4              moltype = DNA  length = 20
FEATURE                   Location/Qualifiers
misc_feature              1..20
                          note = The sequence is synthesized.
source                    1..20
                          mol_type = other DNA
                          organism = synthetic construct
SEQUENCE: 4
atgaagattt tcagttgggt                                               20

SEQ ID NO: 5              moltype = DNA  length = 20
FEATURE                   Location/Qualifiers
misc_feature              1..20
                          note = The sequence is synthesized.
source                    1..20
                          mol_type = other DNA
                          organism = synthetic construct
```

```
SEQUENCE: 5
ttacatttcg agcacaataa                                                        20

SEQ ID NO: 6             moltype = DNA  length = 38
FEATURE                  Location/Qualifiers
misc_feature             1..38
                         note = The sequence is synthesized.
source                   1..38
                         mol_type = other DNA
                         organism = synthetic construct
SEQUENCE: 6
agatcttcca atactaatga agatttttc agttgggt                                      38

SEQ ID NO: 7             moltype = DNA  length = 35
FEATURE                  Location/Qualifiers
misc_feature             1..35
                         note = The sequence is synthesized.
source                   1..35
                         mol_type = other DNA
                         organism = synthetic construct
SEQUENCE: 7
cggatcccca atactttaca tttcgagcac aataa                                        35

SEQ ID NO: 8             moltype = DNA  length = 20
FEATURE                  Location/Qualifiers
misc_feature             1..20
                         note = The sequence is synthesized.
source                   1..20
                         mol_type = other DNA
                         organism = synthetic construct
SEQUENCE: 8
ggaaagagca tgacggtgaa                                                        20

SEQ ID NO: 9             moltype = DNA  length = 19
FEATURE                  Location/Qualifiers
misc_feature             1..19
                         note = The sequence is synthesized.
source                   1..19
                         mol_type = other DNA
                         organism = synthetic construct
SEQUENCE: 9
gcagtctaag gagcgaggc                                                         19

SEQ ID NO: 10            moltype = DNA  length = 22
FEATURE                  Location/Qualifiers
misc_feature             1..22
                         note = The sequence is synthesized.
source                   1..22
                         mol_type = other DNA
                         organism = synthetic construct
SEQUENCE: 10
gctatcctgt gatctgccct ga                                                     22

SEQ ID NO: 11            moltype = DNA  length = 22
FEATURE                  Location/Qualifiers
misc_feature             1..22
                         note = The sequence is synthesized.
source                   1..22
                         mol_type = other DNA
                         organism = synthetic construct
SEQUENCE: 11
cgccaaactt aataacccag ta                                                     22
```